United States Patent [19]
Weisser

[11] Patent Number: 5,987,152
[45] Date of Patent: *Nov. 16, 1999

[54] METHOD FOR MEASURING VISIBILITY FROM A MOVING VEHICLE

[75] Inventor: Hubert Weisser, Lehre, Germany

[73] Assignee: Volkswagen AG, Wolfsburg, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/972,692

[22] Filed: Nov. 18, 1997

Related U.S. Application Data

[63] Continuation of application No. 08/498,502, Jul. 5, 1995, abandoned.

[30] Foreign Application Priority Data

Jul. 6, 1994 [DE] Germany ............................. 44 23 604

[51] Int. Cl.$^6$ ..................................................... G06K 9/00
[52] U.S. Cl. .......................................... 382/104; 340/937
[58] Field of Search ............................ 340/988; 348/154, 348/155, 169; 364/400; 382/103, 104, 106, 107, 190, 195, 199, 201, 236, 278, 294, 100, 270; 395/1; 701/1, 4, 207, 300–302

[56] References Cited

U.S. PATENT DOCUMENTS

| | | | |
|---|---|---|---|
| 4,216,498 | 8/1980 | Evans et al. | 348/135 |
| 4,969,036 | 11/1990 | Bhanu et al. | 382/236 |
| 5,048,103 | 9/1991 | Leclerc et al. | 382/44 |
| 5,118,180 | 6/1992 | Wichmann et al. | 356/5 |
| 5,179,441 | 1/1993 | Anderson et al. | 348/43 |

FOREIGN PATENT DOCUMENTS

| | | |
|---|---|---|
| 3801368 | 10/1989 | Germany . |
| 3810840 | 11/1989 | Germany . |
| 3735267 | 8/1990 | Germany . |
| 2274368 | 7/1994 | United Kingdom . |

OTHER PUBLICATIONS

Masaki, I., "Three Dimensional Vision System for Intelligent Vehicles", Industrial Electronics, Control and Instrumentation, 1993 Int'l Conference, p. 1712–1717.

Wang, B. et al., "Fuzzy Logic Methods for Image Motion Detection and Analysis", Systems, Man, and Cybernetics, 1993 International Conference, p. 48–52.

"An Efficient and Accurate Camera Calibration Technique for 3D Machine Vision" IEEE 1986, pp. 364–374.

"Computer Image Processing and Recognition", Academic Press, 1979; pp. 77–95.

*Primary Examiner*—Jon Chang
*Assistant Examiner*—Jayanti K. Patel
*Attorney, Agent, or Firm*—Baker & Botts, L.L.P.

[57] ABSTRACT

In a method of measuring visibility from a vehicle in motion, images taken by an optical-electronic camera are transformed into selected image features establishing the loci of defined brightness variations in the images. A range determination of the selected features relative to the optical-electronic camera is carried out followed by filtration of the range readings to establish the prevailing visibility for a vehicle operator or a sensor system based on image processing. The advantage over conventional active methods is that, without requiring an active transmitter, the true visual object contrast as well as the atmospheric transmission enters into the visibility determination.

15 Claims, 3 Drawing Sheets

METHOD FOR MEASURING VISIBILITY FROM A MOVING VEHICLE

This application is a continuation of application Ser. No. 08/498,502, filed on Jul. 5, 1995, now abandoned.

BACKGROUND OF THE INVENTION

This invention relates to methods for measuring visibility from a moving vehicle by image processing techniques.

Most of the information required by a vehicle driver to guide the vehicle is registered visually. The importance of visibility to the driver becomes especially apparent in circumstances in which visibility of the environment to the driver is greatly impaired as, for example, in dense fog or darkness. In a driver's estimate of instantaneous visibility, great errors occur frequently and such errors are aggravated by the absence of reference points such as guideposts at the roadside. But even with such reference points, serious misapprehensions may result because of wide variations in the degree to which the visibility of reference points such as guideposts is impaired because they are faded or soiled. For this reason, the possibility of providing a system for automatic on-board visibility detection in a vehicle is an important consideration. Such a system can be of value not only to assist a human vehicle driver but also for a fully automatic vehicle guidance system.

Various systems for determination of visibility from a vehicle are known in the prior art. For example, German Patent No. DE 37 35 267 describes an arrangement for visibility measurement in which a light emitter, preferably a laser diode, and a light sensor are mounted on a rear-view mirror inside the vehicle. The laser diode produces extremely brief flashes of light aimed though a region of the windshield in the direction of vehicle travel. Depending on the degree to which the windshield is soiled, more or less of the emitted light is diffusely reflected from the windshield. Furthermore, if the vehicle is traveling through a foggy area or approaching a curtain of fog, or if visibility is limited by other matter suspended in the atmosphere, for example smoke, more or less of the light which passes through the windshield is diffusely reflected before it reaches a recognizable object to be detected such as a guidepost.

Light rays reflected back to the sensor by the windshield, the fog or smoke, and the object to be detected, cause the sensor to generate signals representing the level of light intensity picked up from time to time. Moreover, the shorter the visibility, the greater the intensity of the reflected light rays. The arrangement described in this German patent determines the visibility only indirectly, as a function of transmission through the atmosphere, or of the degree to which the windshield is soiled, only those reflected rays which are incident on the sensor being available for analysis.

Another arrangement for determining visibility based on analysis of emitted light rays is disclosed in German Patent No. DE 3,810,840. In that arrangement the physical visibility is determined by using an optical pulsed or continuous radar signal and measuring the range to an object by the transit time method, using parameters of atmospheric transmission, a signal from a brightness sensor, and a searchlight signal. This method is also based chiefly on measuring the proportion of the emitted light which is diffusely reflected by particles present in the atmosphere, and, in darkness, the parameter of brightness enters into the calculation of visibility through the searchlight signal and the brightness sensor. Because the searchlight, especially when stopped down, will not illuminate the roadway space completely, only those objects within the searchlight cone are visible unless an object is intrinsically luminous.

SUMMARY OF THE INVENTION

Accordingly, it is an object of the present invention to provide a method for measuring visibility from a moving vehicle which overcomes the disadvantages of the prior art.

Another object of the invention is to provide a method for measuring visibility that will produce accurate visibility determinations approximating human vision by the use of image processing.

These and other objects of the invention are attained by transforming images taken by a camera arrangement including at least one optical-electronic camera into image parameters characterizing loci of defined brightness variations in the original images. The prevailing visibility is determined by measuring the ranges of the image features relative to the camera arrangement and filtering the range data.

One advantage of this method is that no object recognition is necessary and it is possible to work with only object components. According to a preferred embodiment of the invention, detected image features represent contours of objects or segments of objects, which in turn can be approximated by straight lines or straight-line segments. Because of the quantity of data to be processed, the image features may be limited to distinguishing points on the lines, such as end points or the points of intersection of two lines.

According to one version of the invention, to determine the positions of the detected image features in two images and thus their range from the camera, use is made of a stereo motion method in which the position of the image features in two successive images taken while the vehicle is moving are compared, and a displacement vector is calculated from the differences between the positions of each image feature in the successive images. From the image displacement vector and the known motion of the camera, the position of the object or segment of an object associated with the image feature is determined. The motion of the optical-electronic camera is calculated from known parameters of the motion of the vehicle, such as, for example, the road speed, and the swaying, transverse and/or nodding motion of the vehicle.

According to an advantageous modification of the invention, the optical-electronic camera continuously delivers successive images to be examined for image features at a frequency in the range from 20 to 30 Hz. According to another embodiment, the images produced by the optical-electronic camera are continuous tone images.

The recognition, or detection, of the distinguishing points in the images may advantageously be accomplished by the use of conventional mathematical operators, such as the Moravec operator or the Dreschler operator, which also permit previously determined factors in the drivers' physiological vision system to be included in the threshold calculation.

The prevailing visibility is obtained from the detected ranges of the image features, advantageously using threshold filtering, for example maximum filtering. An important advantage of the method according to the invention over conventional methods is that no active transmitter is required, and the true visual object contrast, in addition to the transmission of the atmosphere, is used in the visibility determination.

BRIEF DESCRIPTION OF THE DRAWINGS

Further objects and advantages of the invention will be apparent from a reading of the following description in conjunction with the accompanying drawings, in which.

DESCRIPTION OF PREFERRED EMBODIMENTS

The principle of the method according to the present invention is based on an analysis of the manner in which human beings collect visual information. Successive images of the same scene received by the eyes are converted into basic image features which merely contain the loci of object alterations from the initial image.

Figure 1:
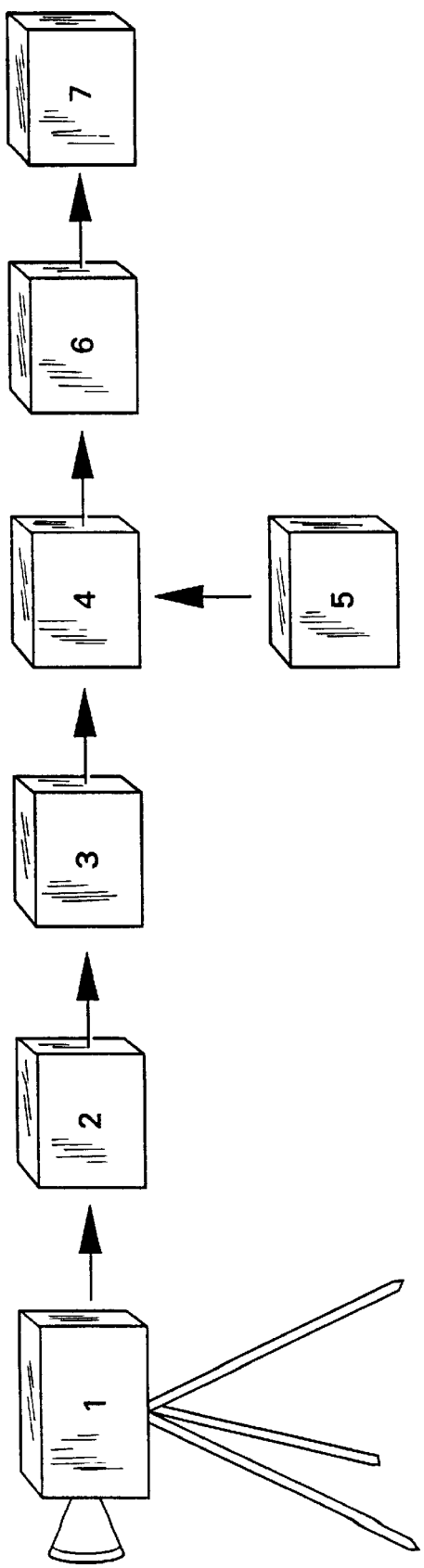
FIG. 1 is a schematic block diagram illustrating the steps of a representative embodiment of the method of the invention.
Figure 2:
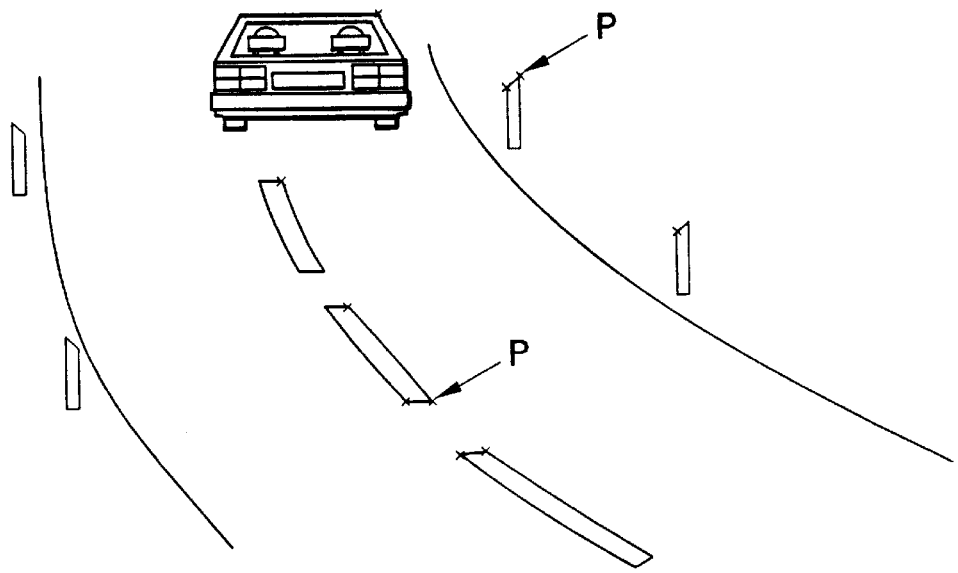
FIG. 2 is a schematic pictorial view showing an image segment with distinguishing points.
Figure 3:
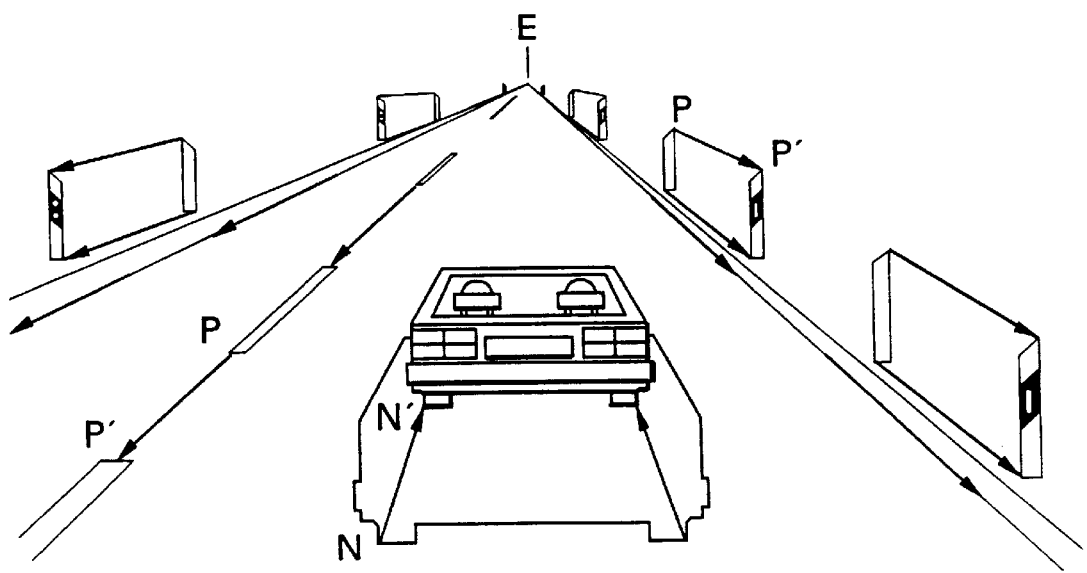
FIG. 3 is a schematic pictorial view showing an image segment with vehicle and object motion displacement vectors.

In the representative embodiment of the invention schematically shown in FIG. 1, a CCD camera 1 is used to produce successive images of a scene viewed from the front of a moving vehicle, delivering continuous tone images at a frequency of 25 Hz. In a succeeding step 2, the images are examined for distinguishing points P, shown in FIG. 2, and the positions of the points P are stored. In the next step 3, the distinguishing points P in a first image are compared with the positions P' of those points in a later image by a stereo motion process. Using the displacement vectors of distinguishing points P thus generated, as shown in FIG. 3, with knowledge of the motion 5 of the vehicle, the position of the distinguishing points P relative to the CCD camera 1 can be calculated in Step 4. In the last step, 6, the data representing the ranges of the distinguishing points are filtered to determine a maximum range, which becomes a measure of the visibility 7.

The individual steps of the method will now be described in more detail. For detection of the distinguishing points P, localized areas or points of the image having a steep brightness autocorrelation function are required, enabling them to be reidentified with certainty in the next image. The Moravec or the modified Moravec operator evaluates localized brightness variations. This operation is carried out as follows. Within a selected image distance from a given image pixel, squares of the gray-scale brightness differences of neighboring pixels are added in various directions. The operator value thus obtained is defined by the minimum of the directional variance and is assigned to the pixel in question. Then all local maxima of the value of the operator that exceed a selected threshold are identified as distinguishing points P. FIG. 2 illustrates an image of an actual roadway scene with identified distinguishing points P.

Another available mathematical operator is the so-called Dreschler operator. The Dreschler operator is effective to detect the differential geometry of the image structures, not in terms of brightness variations but directly in terms of image line curvatures. On the basis of the second derivatives of image component structural variations, the principal or Gaussian curvatures are computed and the distinguishing points P are identified by an interpretation of the local curvature extremes. The result is an accurate characterization of certain features of the image structure.

In Step 3, by comparison of the distinguishing points P and P' in two successive images, a displacement vector field is derived, which permits the actual range determination 4 to be carried out. For this purpose, the corresponding point P' in the second image for each distinguishing point P in the first image is determined, as shown in FIG. 3. The procedure is based on the fact that, when a vehicle is moving in a direction identical with the line of sight, all stationary image points P and P' move radially outward in the field of view toward the edge of the image from an imaginary point E which is the center of expansion. The relative velocity of each point is inversely proportional to its actual distance from the camera. The displacement vectors of the distinguishing points P are thus of various lengths dependent upon the corresponding object positions. Image features of non-stationary objects, for example of other vehicles, generate displacement vectors whose direction does not point radially outward from the center of expansion. This permits stationary and non-stationary objects to be distinguished. FIG. 3 shows the motion vectors of the non-stationary points N with respect to the center of expansion E, as well as those of stationary points P.

Figure 4:
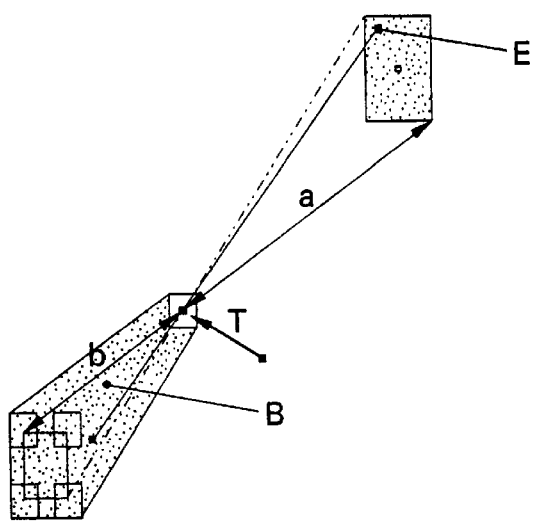
FIG. 4 is a schematic representation of typical search space boundaries.

In determining the range of the stationary distinguishing image points P, account must be taken not only of the radial motion of those points with respect to the center of expansion E but also of the proper motions of the motor vehicle. This is necessary because a CCD camera attached to a vehicle does not point exactly in one direction, i.e., the direction of vehicle travel, but also has additional interfering motion components as a result of nodding and swaying motions of the vehicle. For this reason, regions of uncertainty are introduced both around the center of expansion E and around the distinguishing points P. In this connection, it must be kept in mind that the detected position of each distinguishing point P must be changed from the first image to the second image, and this is effected by a translation vector T emanating from the original point P. To locate the displaced point P' a search space around the point P is determined from the predicted motion of the stationary points and the regions of uncertainty. Since points P located near the center of expansion E have smaller displacement vectors than points farther away, the search space length b, shown in FIG. 4, is controlled in accordance with the distance a from the distinguishing point P to the center of expansion E. This procedure not only reduces the number of distinguishing points required for correlation but also effects a special filtration to identify stationary points. This is necessary because non-stationary points are of no value in determining position by a stereo motion process, since their change of actual position between images is, in general, not known.

Each distinguishing point P' in the second image that lies within the search space for a point P as defined above is a potential candidate for the corresponding point P identified in the first image. The decision which distinguishing point in the second image corresponds to the distinguishing point in the first image can be made with the aid of conventional "fuzzy" logic algorithms. Input variables that may be used in the fuzzy logic inference system include:

1. The position distinguishing points P and P' with respect to the search space;
2. The number of distinguishing points;
3. The maximum of the Gaussian distribution curve;
4. The structural evolution of the Dreschler operator;
5. The number of corresponding minima in the Dreschler operator;
6. The mean brightness value of the environment; and
7. Transgression of a minimum threshold.

The fourth item noted above concerns a special behavior of the Dreschler operator. Very small, approaching pinpoint, image elements consist of a maximum of the Gaussian distribution surround by several minima. If these elements are enlarged, as occurs when one moves closer, they become more pronounced, with the result that the number of minima surrounding the maximum decreases, in the extreme case to one minimum. Using this effect, it can be determined that a camera is moving toward the point of interest.

In carrying out the above-mentioned fuzzy logic analysis, each distinguishing point P' in the second image which is located within the search space B shown in FIG. 4 is assigned a rating for resemblance to a corresponding distinguishing point P in the first image. The identification of a point P' corresponding to each point P results in the determination of displacement vectors for stationary points in the scene due to the change in position of the camera.

From the displacement vectors for stationary distinguishing points P, determined by the spacing of pairs of corresponding points P and P', and taking into account the yawing, nodding and swaying motion of the vehicle, the ranges of the objects or object components pertaining to the distinguishing points P are calculated and plotted in a range histogram. Since in this example the vehicle and the CCD camera approached the distinguishing point P while the images were being taken, this range calculation is to be referred to the distinguishing points P' in the second image.

Figure 5A:
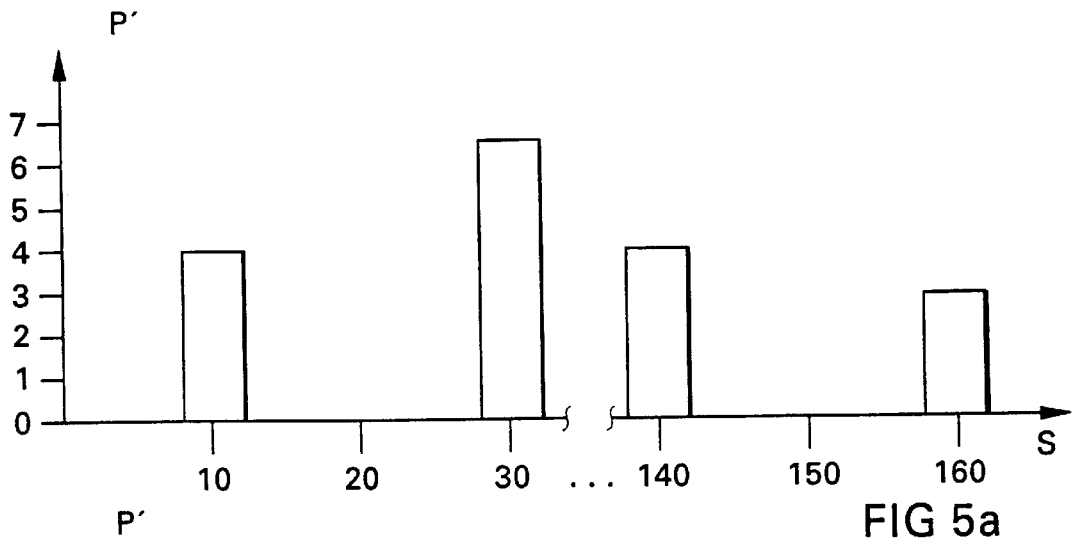
FIGS. 5a and 5b illustrate typical object range histograms.
Figure 5B:
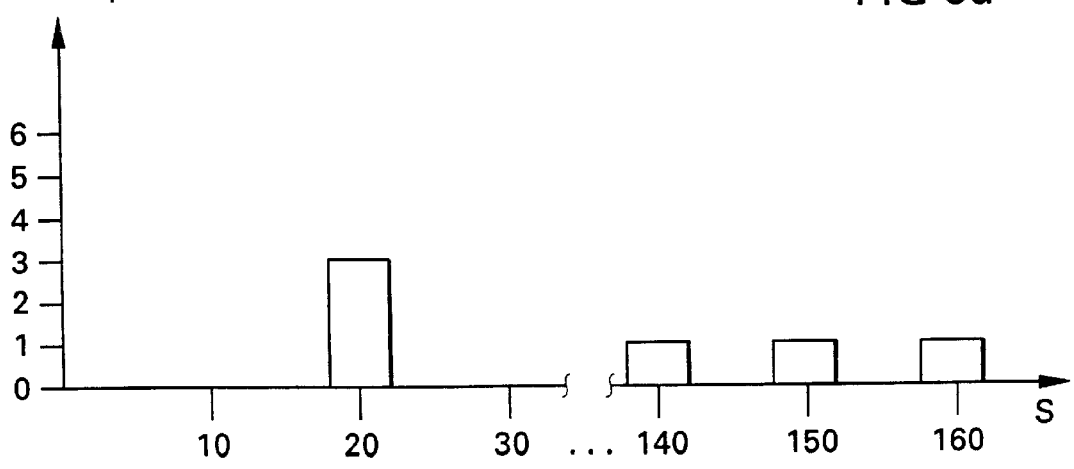

In the next step of the method, the visibility is determined from the range distribution of the objects pertaining to the distinguishing points which were detected, whose photometric contrast is therefore greater than a defined threshold, for example the physiological threshold of contrast for the human eye. Since the order of magnitude of the visibility is far more important than an exact value, the visibility determination in this typical embodiment is made at intervals of the object ranges of 10 m. The cycle of evaluation therefore takes place by an organization of range intervals having a local low-pass characteristic, i.e. 10 m, reducing fluctuations in the result. Thus, for each object point detected, the value of the corresponding range interval is incremented, and then a maximum filtration is performed. To exclude accidental errors, this step selects either the highest range interval having a point frequency greater than 1 or a range interval having a point frequency of at least 1 with the next two lower neighboring fields occupied. A range histogram for a visibility of 160 meters satisfying the first criterion is shown in FIG. 5a and one satisfying the second criterion is shown in FIG. 5b.

Although the invention has been described herein with reference to specific embodiments, many modifications and variations therein will readily occur to those skilled in the art. For example, instead of using image data from two successive images taken by the same camera during vehicle motion, image data from two simultaneous images taken by laterally spaced cameras could be used. In that case ranges would be based on displacement vectors determined by triangulation rather than motion vectors. Accordingly, all such variations and modifications are intended to be included within the scope of the invention.

I claim:

1. A method of measuring visibility to an operator of a vehicle in motion while the vehicle is in motion comprising producing a plurality of images of a scene viewed by an operator of the vehicle in the direction of the visibility to be measured using optical-electronic camera means, comprising the loci in successive images of the plurality of selected image features of defined local brightness contrast in stationary objects in the images, determining the ranges of distances of the selected image features in the scene relative to the optical-electronic camera means, and determining the visibility to an operator of the vehicle based upon the ranges of the selected image features in the scene by way of a maximum range filtration using a threshold value for the brightness contrast of the selected image features.

2. A method according to claim 1 wherein selected image features are contours of objects in the scene.

3. A method according to claim 1 wherein the selected image features are straight lines or straight line segments of approximated contours in the image.

4. A method according to claim 3 wherein the straight lines or straight line segments are defined by distinguishing points on the lines or line segments.

5. A method according to claim 4 wherein the ranges of selected image features in a scene from the optical-electronic camera means are determined by comparing the positions of the distinguishing points in two images taken from different positions, computing displacement vectors from the differences in the positions of the distinguishing points in the images, and determining the positions in the scene of the objects or object segments corresponding to the distinguishing points.

6. A method according to claim 5, wherein the optical-electronic camera means includes two cameras spaced transversely with respect to the direction of motion and the two images of the scene which are compared are taken simultaneously by the two cameras.

7. A method according to claim 5 wherein two images of the scene which are compared are taken successively by a single optical-electronic camera which is moved.

8. A method according to claim 7 wherein the amount of motion of the optical-electronic camera is computed from the vehicle road speed and one or more of a swaying, transverse, and nodding motion of the vehicle.

9. A method according to claim 4 wherein the selection of the distinguishing points from the images takes place by way of one or more Moravec operators.

10. A method according to claim 4 wherein selection of the distinguishing points from the images takes place by way of one or more Dreschler operators.

11. A method according to claim 1 wherein the electronic camera means continuously produces images of the scene at a frequency in the range from 20 to 30 Hz.

12. A method according to claim 1 wherein the optical-electronic camera means produces continuous tone images.

13. A method according to claim 1 wherein a mathematical operator is used to select distinguishing image points and parameters of a driver's physiological vision are used in a mathematical transformation.

14. A method according to claim 1 wherein fuzzy logic algorithms are used to identify an image feature of a first image in a second image.

15. A method according to claim 1 including determining the range of measurement of a sensor system based on image processing.

* * * * *